US009090587B2

(12) United States Patent
Araya et al.

(10) Patent No.: US 9,090,587 B2
(45) Date of Patent: Jul. 28, 2015

(54) 7-{(3S,4S)-3-[(CYCLOPROPYLAMINO)METHYL]-4-FLUOROPYRROLIDINE-1-YL}-6-FLUORO-1-(2-FLUORODETHYL)-ACID CRYSTAL

(71) Applicant: KYORIN PHARMACEUTICAL CO., LTD, Tokyo (JP)

(72) Inventors: Ichiro Araya, Tochigi (JP); Akinori Goto, Tochigi (JP); Wataru Minagawa, Tochigi (JP); Keiko Funada, Tochigi (JP); Muneki Nagao, Tochigi (JP)

(73) Assignee: KYORIN PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/352,141

(22) PCT Filed: Nov. 9, 2012

(86) PCT No.: PCT/JP2012/007195
§ 371 (c)(1),
(2) Date: Apr. 16, 2014

(87) PCT Pub. No.: WO2013/069297
PCT Pub. Date: May 16, 2013

(65) Prior Publication Data
US 2014/0288310 A1  Sep. 25, 2014

(30) Foreign Application Priority Data

Nov. 10, 2011  (JP) ................................. 2011-246209
Mar. 27, 2012  (JP) ................................. 2012-071739

(51) Int. Cl.
C07D 401/04      (2006.01)
A61K 31/4709    (2006.01)

(52) U.S. Cl.
CPC ........... *C07D 401/04* (2013.01); *A61K 31/4709* (2013.01)

(58) Field of Classification Search
CPC .......................... C07D 401/04; A61K 31/4709
USPC ....................................................... 546/159
See application file for complete search history.

(56) References Cited

U.S. PATENT DOCUMENTS

2006/0281779 A1  12/2006  Asahina et al.

FOREIGN PATENT DOCUMENTS

| CN | 1158846 | 9/1997 |
| JP | 2005-502861 | 1/2005 |
| WO | 03/014732 | 2/2003 |
| WO | 03/076428 | * 9/2003 |
| WO | 2005/026147 | 3/2005 |
| WO | 2007/082471 | 7/2007 |

OTHER PUBLICATIONS

International Search Report issued Feb. 19, 2013 in International (PCT) Application No. PCT/JP2012/007195.
English translation of the International Preliminary Report on Patentability and Written Opinion dated May 13, 2014.
Noriyuki Takata, "API form screening and selection in drug discovery stage", Pharm Stage, 2007, vol. 6, No. 10, pp. 20-25.
Hiroshi Ooshima, "Crystallization of Polymorphs and Pseudopolymorphs and Its Control", Pharm Stage, 2007, vol. 6, No. 10, pp. 48-53.
Takashi Kojima et al., "Effective selection of crystal form in pharmaceutical development Application of Raman spectroscopy to salt and polymorph screenings", Pharm Tech Japan, 2007, vol. 23, No. 12, pp. 173(2461)-181(2469).
P. Stahly, Journal of Pharmaceutical Science and Technology, Japan, 2006, vol. 66, No. 6, pp. 435-439.
R.J. Bastin et al., "Salt Selection and Optimization Procedures for Pharmaceutical New Chemical Entities", Organic Process Research & Development, 2000, vol. 4, No. 5, pp. 427-435.
Takashi Kojima et al., Journal of Pharmaceutical Science and Technology, Japan, 2007, vol. 67 supplement, p. 426.
Mitsuo Matsumoto et al. (Eds.), Manual for Pharmaceutical Science, 1989, First edition, Nanzando, p. 28.
Pharmaceutical Affairs Bureau Notification No. 568, May 1, 2001.
Decision of Refusal issued May 26, 2015 in corresponding Japanese Patent Application No. 2013-542858.

* cited by examiner

Primary Examiner — D M Seaman
(74) Attorney, Agent, or Firm — Wenderoth, Lind & Ponack, L.L.P.

(57) ABSTRACT

Disclosed is a technique for improving the water solubility and storage stability of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid (compound (1)) that is safe and not only has a strong antibacterial action but also is effective for resistant bacteria for which conventional antibacterial agent are less effective. Crystals of the hydrochloride salt of the compound (1), crystals of the hydrochloride salt hydrate of the compound (1), and crystals of the methanesulfonate salt of the compound (1) are provided. In these crystals, decomposition due to influences of light is suppressed as compared to that in crystals of the compound (1) in free, and their storage stability is high. These crystals have higher solubility in water than the crystals of the compound (1) in free.

47 Claims, 3 Drawing Sheets

7-{(3S,4S)-3-[(CYCLOPROPYLAMINO)METHYL]-4-FLUOROPYRROLIDINE-1-YL}-6-FLUORO-1-(2-FLUORODETHYL)-ACID CRYSTAL

FIELD

The present invention relates to crystals of salts of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid (hereinafter may be referred to as a compound (1)) represented by a formula (1) and to methods for producing these crystals.

[Chemical formula 1]

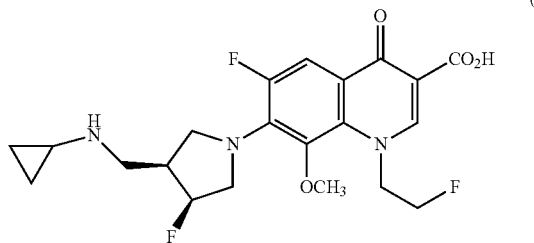

(1)

BACKGROUND

Generally, requirements for pharmaceutical products include safety, quality, etc. as well as therapeutic effects on diseases. Therefore, compounds serving as active components of pharmaceutical products are required to have high storage stability under various conditions (light, temperature, humidity, etc. have influences on the compounds). When a pharmaceutical product is in the form of oral dosage formulation or injection, it is preferable for an active component contained in the pharmaceutical product to have high solubility in water.

It is known that the compound (1) not only is safe and has a strong antibacterial action but also exhibits a strong antibacterial activity against gram-positive bacteria, particularly resistant bacteria such as MRSA, PRSP, and VRE, for which conventional antibacterial agents are less effective (for example, Patent Literature 1).

CITATION LIST

Patent Literature

Patent Literature 1: WO2005/026147 pamphlet

SUMMARY

Technical Problem

Patent Literature 1 only shows that the compound (1) has physicochemical features that the compound is in free, forms of light brown crystals. Patent Literature 1 discloses no information about the solubility of the compound (1) in water, its stability, the features of its crystals, etc.

It is an object of the present invention to provide a technique capable of improving the solubility of the compound (1) in water and its storage stability.

Solution to Problem

The present inventors conducted research and development on a method for producing the compound (1) which is useful as an antibacterial agent and found that crystals of the compound (1) in free (hereinafter may also be simply referred to as free crystals) obtained by the method described in Patent Literature 1 had low solubility in water and poor storage stability against light. Therefore, it was considered to be difficult to obtain crystals having high solubility in water and high storage stability using the method in Patent Literature 1.

To solve the foregoing problem, the present inventors conducted extensive studies on the compound (1) and the method of producing the same. As a result of the studies, the inventors found that crystals of the hydrochloride salt of the compound (1) and crystals of the methanesulfonate salt of the compound (1) had high solubility and storage stability. The inventors also found methods for producing homogeneous crystals of the hydrochloride salt of the compound (1) and homogeneous crystals of the methanesulfonate salt of the compound (1) in a commercial scale.

More specifically, the present inventors tried to make a hydrochloride salt of the compound (1) from the compound (1) in free obtained by the method in Patent Literature 1 and thereby obtained a crude hydrochloride salt. Then the obtained crude hydrochloride salt was subjected to crystallization treatment (recrystallization) to obtain crystals of the hydrochloride salt.

The inventors evaluated the physical properties of the obtained hydrochloride salt crystals and found that there were three novel types of hydrochloride salt crystals (crystals A, crystals B, and crystals C) and a plurality of pseudomorphouscrystal forms.

In the obtained crystals, a reduction in purity (decomposition) due to influences of temperature and humidity was more suppressed in the crystals A and B than in the crystals C and the plurality of pseudomorphouscrystal forms, and therefore the crystals A and B were found to have very high storage stability against temperature and humidity.

As for the storage stability against light, the crystals A were more stable than the free crystals.

The inventors conducted detailed studies on the crystals A and B and found that the crystals A were an anhydrous of the hydrochloride salt of the compound (1) and the crystals B were a hydrate of the hydrochloride salt of the compound (1).

The inventors also conducted studies on methods for producing the hydrochloride salt crystals. The inventors found that the crystals A and B could be selectively produced in an efficient manner by controlling the amount of a solvent (crystallization solvent) used in the crystallization treatment for obtaining purified crystals, particularly the amount of water in the crystallization solvent.

The inventors also tried to make the methanesulfonate salt of the compound (1) from the compound (1) in free obtained by the method in Patent Literature 1 with methanesulfonic acid and thereby obtained a crude methanesulfonate salt. Then the obtained crude methanesulfonate salt was subjected to crystallization treatment (recrystallization) to obtain crystals of the methanesulfonate salt.

A reduction in purity (decomposition) due to influences of temperature and humidity was more suppressed in the obtained crystals of the methanesulfonate salt than in the crystals C, as in the crystals A and B, and the obtained crystals of the methanesulfonate salt were found to have very high storage stability against temperature and humidity. As for the storage stability against light, the crystals of the methanesulfonate salt were more stable than the free crystals.

The crystals A and B and the crystals of the methanesulfonate salt had higher solubility in water than the free crystals.

Accordingly, the present invention includes the following aspects.

[1] A crystal of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt, having powder X-ray diffraction peaks at diffraction angles 2θ of 10.8°±0.2°, 12.9°±0.2°, and 24.7°±0.2°.

[2] The crystal according to [1], having powder X-ray diffraction peaks at diffraction angles 2θ of 4.9°±0.2°, 10.8°±0.2°, 12.9°±0.2°, 18.2°±0.2°, 21.7°±0.2°, 24.7°±0.2°, and 26.4°±0.2°.

[3] The crystal according to [1] or [2], having a powder X-ray diffraction pattern identical to a powder X-ray diffraction pattern shown in FIG. 1.

[4] The crystal according to any one of [1] to [3], wherein, in differential thermal analysis (DTA), an exothermic peak appears only in the vicinity of 210° C., and in thermogravimetric (TG) analysis, no weight loss occurs below 100° C.

[5] A crystal of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt hydrate, having powder X-ray diffraction peaks at diffraction angles 2θ of 9.4°±0.2° and 17.7°±0.2°.

[6] The crystal according to [5], having powder X-ray diffraction peaks at diffraction angles 2θ of 4.8°±0.2°, 9.4°±0.2°, 17.7°±0.2°, 22.8°±0.2°, 25.8°±0.2°, and 27.0°±0.2°.

[7] The crystal according to [5] or [6], having a powder X-ray diffraction pattern identical to a powder X-ray diffraction pattern shown in FIG. 2.

[8] The crystal according to any one of [5] to [7], wherein, in differential thermal analysis (DTA), an endothermic peak appears between room temperature and 100° C., and an exothermic peak appears in the vicinity of 140° C., and in thermogravimetric (TG) analysis, weight loss until 100° C. is about 7%.

[9] The crystal according to any one of [5] to [8], wherein a water content determined by Karl Fischer water content determination is about 7%.

[10] A crystal of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid methanesulfonate salt, having powder X-ray diffraction peaks at diffraction angles 2θ of 9.9°±0.2°, 14.1°±0.2°, and 28.0°±0.2°.

[11] The crystal according to [10], having powder X-ray diffraction peaks at diffraction angles 2θ of 9.9°±0.2°, 14.1°±0.2°, 16.6°±0.2°, 19.8°±0.2°, 22.3°±0.2°, and 28.0°±0.2°.

[12] The crystal according to [10] or [11], having a powder X-ray diffraction pattern identical to a powder X-ray diffraction pattern shown in FIG. 3.

[13] The crystal according to anyone of [10] to [12], wherein, in differential thermal analysis (DTA), an endothermic peak appears in the vicinity of 213° C., and an exothermic peak appears only in the vicinity of 220° C., and in thermogravimetric (TG) analysis, no weight loss occurs below 100° C.

[14] A pharmaceutical comprising the crystal according to any one of [1] to [13].

[15] An antibacterial agent comprising the crystal according to any one of [1] to [13], or prepared by incorporating the crystal according to any one of [1] to [13] as an active pharmaceutical ingredient.

[16] The antibacterial agent according to [15], wherein the antibacterial agent is an oral dosage formulation.

[17] The antibacterial agent according to [15], wherein the antibacterial agent is an injection.

[18] A method for producing the crystal according to any one of [1] to [4], comprising:
adding hydrochloric acid to a 2-propanol solution of 7-{(3S,4S)-3-[(cyclopropylamino)methyl]-4-fluoropyrrolidine-1-yl}-6-fluoro-1-(2-fluoroethyl)-8-methoxy-4-oxo-1, 4-dihydroquinoline-3-carboxylic acid to obtain a crude hydrochloride salt; and
crystallizing the obtained crude hydrochloride salt with hydrous ethanol having a water activity of less than 0.5 or hydrous 2-propanol having a water activity of less than 0.5.

[19] A crystal obtained by: adding hydrochloric acid to a 2-propanol solution of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid to obtain a crude hydrochloride salt; and crystallizing the obtained crude hydrochloride salt with hydrous ethanol having a water activity of less than 0.5 or hydrous 2-propanol having a water activity of less than 0.5.

[20] A method for producing the crystal according to any one of [5] to [9], comprising:
adding hydrochloric acid to a 2-propanol solution of 7-{(3S,4S)-3-[(cyclopropylamino)methyl]-4-fluoropyrrolidine-1-yl}-6-fluoro-1-(2-fluoroethyl)-8-methoxy-4-oxo-1, 4-dihydroquinoline-3-carboxylic acid to obtain a crude hydrochloride salt; and
crystallizing the obtained crude hydrochloride salt with hydrous ethanol having a water activity of 0.5 or higher or hydrous 2-propanol having a water activity of 0.5 or higher.

[21] A crystal obtained by: adding hydrochloric acid to a 2-propanol solution of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid to obtain a crude hydrochloride salt; and crystallizing the obtained crude hydrochloride salt with hydrous ethanol having a water activity of 0.5 or higher or hydrous 2-propanol having a water activity of 0.5 or higher.

[22] A method of producing the crystal according to any one of [10] to [13], comprising:
adding methanesulfonic acid to an acetone solution of 7-{(3S,4S)-3-[(cyclopropylamino)methyl]-4-fluoropyrrolidine-1-yl}-6-fluoro-1-(2-fluoroethyl)-8-methoxy-4-oxo-1, 4-dihydroquinoline-3-carboxylic acid to obtain a crude methanesulfonate salt; and
crystallizing the obtained crude methanesulfonate salt with hydrous acetone.

[23] A crystal obtained by: adding methanesulfonic acid to an acetone solution of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid to obtain a crude methanesulfonate salt; and crystallizing the obtained crude methanesulfonate salt with hydrous acetone.

Advantageous Effects of Invention

According to the present invention, a technique capable of improving the solubility of the compound (1) in water and the storage stability of the compound (1) can be provided.

DESCRIPTION OF EMBODIMENTS

Crystals of the hydrochloride salt of the compound (1) (crystals A) in the present embodiment can be produced by, for example, the following method.

Specifically, the compound (1) in free is dissolved in 2-propanol as a solvent. Hydrochloric acid is added to the obtained 2-propanol solution of the compound (1) to make a hydrochloride salt of the compound (1), and a crude hydrochloride salt is thereby generated. The crude hydrochloride salt of the compound (1) can be separated from the solvent by, for example, filtration.

Then the obtained crude hydrochloride salt is subjected to crystallization treatment (recrystallization) using hydrous ethanol or hydrous 2-propanol each having a water activity of less than 0.5 as a crystallization solvent, and the crystals A can thereby be selectively obtained. The crystallization solvent is preferably hydrous ethanol or hydrous 2-propanol each having a water activity of 0.3 or higher and less than 0.5 and more preferably hydrous ethanol having a water activity of 0.3 or higher and less than 0.5. Still more preferably, the crystallization solvent is hydrous ethanol having a water activity of 0.3 or higher and 0.43 or less.

The hydrous ethanol as used herein is a solvent mixture of water and ethanol. The hydrous 2-propanol as used herein is a solvent mixture of water and 2-propanol.

The water activity (aw) as used herein is defined as the ratio of the pressure (P) of water vapor in a closed vessel to the vapor pressure (PO) of pure water at the temperature of the water vapor and is determined by the following formula (i).

$$aw = P/PO \quad (i)$$

In a gas phase, i.e., in air, the water activity corresponds to a value obtained by dividing a relative humidity (%) by 100. For example, a relative humidity of 75% corresponds to a water activity of 0.75. It is well-known that the water activity of a solution mixture of an organic solvent and water varies depending on the concentration of water and the miscibility between the solvent and water and is generally nonlinear. The value of the water activity of a solution mixture of an organic solvent and water can be obtained from well-known chemical and physical reference databases.

The compound (1) in free can be produced, for example, by the method described in Patent Literature 1.

The crystals A exhibit a powder X-ray diffraction pattern with peaks at diffraction angles 2θ of 10.8°±0.2°, 12.9°±0.2°, and 24.7°±0.2°. Specifically, the crystals A exhibit a powder X-ray diffraction pattern with peaks at 4.9°±0.2°, 10.8°±0.2°, 12.9°±0.2°, 18.2°±0.2°, 21.7°±0.2°, 24.7°±0.2°, and 26.4°±0.2°.

Figure 1:
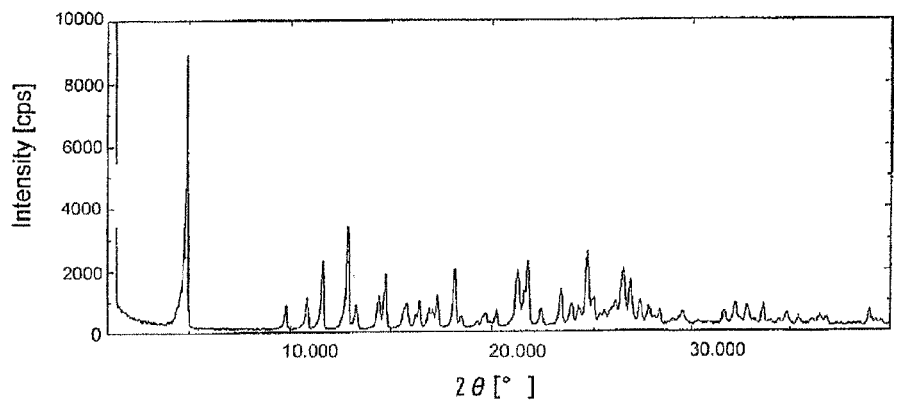
FIG. 1 shows a powder X-ray diffraction pattern of the hydrochloride salt of the compound (1) (crystals A).

More specifically, the crystals A exhibit a powder X-ray diffraction pattern identical to, for example, a powder X-ray diffraction pattern shown in FIG. 1.

In differential thermal analysis (DTA), the crystals A exhibit an exothermic peak due to decomposition only in the vicinity of 210° C. In thermogravimetric (TG) analysis, the crystals A exhibit no weight loss below 100° C.

The powder X-ray diffraction can be performed using, for example, RINT2200 manufactured by Rigaku Corporation. Copper radiation can be used as radiation, and the measurement can be performed under the conditions of a tube current of 36 mA, a tube voltage of 40 kV, a divergence slit of 1°, a scattering slit of 1°, a receiving slit of 0.15 mm, a scan range of 1 to 40° (2θ), and a scan rate of 2° (2θ)/min.

The differential thermal analysis (DTA) and the thermogravimetric (TG) analysis can be performed using, for example, TG/DTA6200 manufactured by Seiko Instruments Inc. The measurement can be performed, for example, in a dry nitrogen atmosphere under the measurement conditions of a temperature of from 30° C. to 250° C. at a temperature rise rate of 5° C./rain. The differential thermal analysis (DTA) and the thermogravimetric (TG) analysis are also referred to as thermal analysis (TG/DTA).

Crystals of a hydrate of the hydrochloride salt of the compound (1) (crystals B) in the present embodiment can be produced by, for example, the following method.

Specifically, the compound (1) in free is dissolved in 2-propanol as a solvent. Hydrochloric acid is added to the obtained 2-propanol solution of the compound (1) to make a hydrochloride salt of the compound (1), and a crude hydrochloride salt is thereby generated. The crude hydrochloride salt of the compound (1) can be separated from the solvent by, for example, filtration.

Then the obtained crude hydrochloride salt of the compound (1) is subjected to crystallization treatment using hydrous ethanol or hydrous 2-propanol each having a water activity of 0.5 or higher as a crystallization solvent, and the crystals B can thereby be selectively obtained. The crystallization solvent is preferably hydrous ethanol or hydrous 2-propanol each having a water activity of 0.5 or higher and 0.8 or less and more preferably hydrous 2-propanol having a water activity of 0.5 or higher and 0.8 or less. Still more preferably, the crystallization solvent is hydrous 2-propanol having a water activity of 0.52 or higher and 0.77 or less.

The crystals B exhibit a powder X-ray diffraction pattern with peaks at diffraction angles 2θ of 9.4°±0.2° and 17.7°±0.2°. Specifically, the crystals B exhibit a powder X-ray diffraction pattern with peaks at 4.8°±0.2°, 9.4°±0.2°, 17.7°±0.2°, 22.8°±0.2°, 25.8°±0.2°, and 27.0°±0.2°. More specifically, the crystals B exhibit a powder X-ray diffraction pattern identical to, for example, a powder X-ray diffraction pattern shown in FIG. 2.

In differential thermal analysis (DTA), the crystals B exhibit an endothermic peak due to dehydration during temperature rise from room temperature to 100° C. and an exothermic peak in the vicinity of 140° C. In thermogravimetric (TG) analysis, the crystals B exhibit a weight loss of about 7% until 100° C. The crystals B have a water content of about 7% as determined by Karl Fischer water content determination.

The Karl Fischer water content determination can be performed using, for example, MKS-510N manufactured by Kyoto Electronics Manufacturing Co., Ltd. The measurement can be performed by a titration method.

The crystals B can be converted to the crystals A, which are the crystals of the anhydrous of the hydrochloride salt of the compound (1), by drying the crystals B at a temperature of 30° C. or higher and a reduced pressure of 100 hPa or less.

Crystals of the methanesulfonate salt of the compound (1) in the present embodiment can be produced by, for example, the following method.

Specifically, the compound (1) in free are dissolved in acetone as a solvent. Methanesulfonic acid is added to the obtained acetone solution of the compound (1) to satisfy the compound (1), and a crude methanesulfonate salt is thereby generated. The crude methanesulfonate salt can be separated from the solvent by, for example, filtration.

Then the obtained crude methanesulfonate salt of the compound (1) is subjected to crystallization treatment using hydrous acetone as a crystallization solvent, and the crystals of the methanesulfonate salt of the compound (1) can thereby be selectively obtained. The hydrous acetone as used herein is a solvent mixture of water and acetone. The volume ratio of acetone and water is preferably 4:1 to 6:1 and more preferably 5:1.

In powder X-ray diffraction, the crystals of the methanesulfonate salt of the compound (1) exhibit a powder X-ray diffraction pattern with peaks at diffraction angles 2θ of 9.9°±0.2°, 14.1°±0.2°, and 28.0°±0.2°. Specifically, the crystals exhibit a powder X-ray diffraction pattern with peaks at 9.9°±0.2°, 14.1°±0.2°, 16.6°±0.2°, 19.8°±0.2°, 22.3°±0.2°, and 28.0°±0.2°. More specifically, the methanesulfonate salt of the compound (1) exhibits a powder X-ray diffraction pattern identical to, for example, a powder X-ray diffraction pattern shown in FIG. 3.

In differential thermal analysis (DTA), the crystals of the methanesulfonate salt of the compound (1) exhibit an endothermic peak due to melting in the vicinity of 213° C. and an exothermic peak due to decomposition only in the vicinity of 220° C. In thermogravimetric (TG) analysis, the crystals exhibit no weight loss below 100° C.

In one embodiment, a pharmaceutical containing the crystal A, the crystal B, or the crystal of the methanesulfonate salt of the compound (1) can be formed. For example, the pharmaceutical in this embodiment may be formed as a pharmaceutical composition containing, as an active ingredient, the crystal A, the crystal B, or the crystal of the methanesulfonate salt of the compound (1) and further containing other ingredients such as a pharmaceutically acceptable carrier, solvent, and diluent.

The crystals relating to the present embodiments exhibit a strong antibacterial activity against gram-positive bacteria, particularly resistant bacteria such as MRSA, PRSP, and VRE, and are highly safe. In an embodiment, an antibacterial agent containing, as an active ingredient, a crystal of the compound (1) relating to the present embodiments or an antibacterial agent prepared by incorporating a crystal of the compound (1) relating to the present embodiments as an active pharmaceutical ingredient can be formed. Specifically, for example, the antibacterial agent comprises, the crystal A, the crystal B, or the crystal of the methanesulfonate salt of the compound (1) as an active ingredient and further containing other ingredients such as a pharmaceutically acceptable carrier, solvent, and diluent.

Also, for example, the antibacterial agent is prepared by incorporating the crystal A, the crystal B, or the crystal of the methanesulfonate salt of the compound (1) as an active ingredient with other ingredients such as a pharmaceutically acceptable carrier, solvent, and diluent. No particular limitation is imposed on the form of the antibacterial agent. Examples of the form of the antibacterial agent include: oral dosage formulations such as powders, tablets, capsules, syrups, and liquors; injections; ointments; eye lotions; and suppositories. The antibacterial agent is preferably in the form of oral dosage formulation or injection. When the antibacterial agent is in the form of oral dosage formulation or injection, no particular limitation is imposed on the amount added of the crystals of the compound (1), but the amount is 0.001 to 98%. When the antibacterial agent is in the form of oral dosage formulation, the amount added of the crystals of the compound (1) is preferably 50 to 90%. When the antibacterial agent is in the form of injection, the amount added of the crystals of the compound (1) is preferably 0.01 to 1%.

In the crystals relating to the present embodiments, decomposition due to influences of light is suppressed as compared to that in the free crystals, and therefore the crystals relating to the present embodiments exhibit high storage stability. The crystals relating to the present embodiments have higher solubility in water than the free crystals. Therefore, according to the present embodiments, crystals of salts of the compound (1) that are useful as active pharmaceutical ingredients of pharmaceuticals can be provided.

According to the methods for producing the crystals A and B exemplified in the present embodiments, the crystals A and B can be selectively produced in an efficient manner. Therefore, these methods can further contribute to the provision of the crystals of the salts of the compound (1) that are useful as active pharmaceutical ingredients of pharmaceuticals.

The present invention will next be described in more detail by way of examples, but the invention is not limited to these examples.

A melting point was measured using a Yanagimoto micro-melting point apparatus MP-500D. An IR spectrum was measured using an infrared spectrophotometer of the type Nicolet6700 manufactured by Thermo Fisher Scientific K.K. An NMR spectrum was measured using a nuclear magnetic resonance apparatus of the type JNM-EX400 manufactured by JEOL Ltd. with tetramethyl silane (TMS) as the internal standard. An MS spectrum was measured using mass spectrometers of the types JMS-T100LP and JMS-SX102A manufactured by JEOL Ltd. An elementary analysis was performed using an elementary analysis apparatus of CHN CORDER MT-6 manufactured by yaic.yanaco. A specific rotation was measured using DIP-370 manufactured by JASCO Corporation.

Powder X-ray diffraction was performed using RINT2200 manufactured by Rigaku Corporation. Copper radiation can be used as radiation, and the measurement was performed under the conditions of a tube current of 36 mA, a tube voltage of 40 kV, a divergence slit of 1°, a scattering slit of 1°, a receiving slit of 0.15 mm, a scan range of 1 to 40° (2θ), and a scan rate of 2° (2θ)/min.

Differential thermal analysis (DTA) and thermogravimetric (TG) analysis were performed using TG/DTA6200 manufactured by Seiko Instruments Inc. The measurement was performed in a dry nitrogen atmosphere under the measurement conditions of a temperature of from 30° C. to 250° C. at a temperature rise rate of 5° C./min.

Karl Fischer water content determination was performed using MKS-510N manufactured by Kyoto Electronics Manufacturing Co., Ltd. The measurement was performed by a titration method.

REFERENCE EXAMPLE 1

7-{(3S,4S)-3-[(cyclopropylamino)methyl]-4-fluoro-pyrrolidine-1-yl}-6-fluoro-1-(2-fluoroethyl)-8-methoxy-4-oxo-1,4-dihydroquinoline-3-carboxylic acid hydrochloride salt A solution mixture (which may also be referred to as a reaction mixture) of 3.56 kg (15.4 mol) of (3R,4S)-3-cyclopropylaminomethyl-4-fluoropyrrolidine, 11.7 L (84.2 mol) of triethylamine, and 30.0 L of dimethylsulfoxide was stirred at 23.0 to 26.3° C. in a nitrogen atmosphere for 15 minutes. 6.00 kg (14.0 mol) of bis(acetato-O)[6,7-difluoro-1-(2-fluoroethyl)-8-methoxy-4-oxo-1,4-dihydroquinoline-3-carboxylato-$O^3,O^4$]boron was added to the reaction mixture at 23.0 to 26.3° C., and the reaction mixture was stirred at 23.7 to 26.3° C. for 2 hours. 120 L of ethyl acetate was added to the reaction mixture, and 120 L of water was added to the reaction mixture. Then a solution of 960 g of sodium hydroxide (an amount giving a 2 mol/L solution) in 12.0 L of water was added to the reaction mixture. The resultant mixture was stirred for 5 minutes, and an aqueous layer was separated. 120 L of ethyl acetate was added to the aqueous layer, and the mixture was stirred for 5 minutes. Then an ethyl acetate layer was separated.

The ethyl acetate layer was combined, and 120 L of water was added thereto. The mixture was stirred for 5 minutes and left to stand, and an aqueous layer was discarded. Then the ethyl acetate layer was evaporated under reduced pressure. The obtained residue was dissolved in 60.0 L of 2-propanol, and the solution was left to stand overnight at room temperature. A solution of 5.24 L (62.9 mol) of hydrochloric acid in 26.2 L of water (an amount giving a 2 mol/L solution) was added to the solution, and the resultant mixture was stirred at 28.2 to 30.0° C. for 30 minutes. The mixture was heated at an external temperature of 55.0° C. for dissolution (dissolution was observed at 47.1° C.) and then cooled for crystallization. The mixture was stirred at 39.9 to 41.0° C. for 30 minutes, cooled (approximate temperature settings: 7.0° C. until 20.0° C. and −10.0° C. below 20.0° C.), and stirred at 2.2 to 10.0° C. for 1 hour. Precipitated crystals were separated by filtration and washed with 60 L of 2-propanol to obtain 9.57 kg of wet crude crystals of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt.

REFERENCE EXAMPLE 2

7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt hydrate (crystals C)

0.3 mL of hot water at 70° C. was added to 0.02 g (0.04 mmol) of the 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt obtained in Reference Example 1 to dissolve the hydrochloride salt. The solution was allowed to cool to room temperature and left to stand overnight at 5° C. Precipitated crystals were filtrated and dried under reduced pressure to obtain a white powder of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt hydrate (crystals C).

REFERENCE EXAMPLE 3

7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid A solution mixture (which may also be referred to as a reaction mixture) of 142 g (615 mmol) of (3R,4S)-3-cyclopropylaminomethyl-4-fluoropyrrolidine, 274 mL (1,960 mmol) of triethylamine, and 2.40 L of acetonitrile was stirred at an internal temperature of 30 to 35° C. for 0.5 hours. 240 g (559 mmol) of bis(acetato-O)[6,7-difluoro-1-(2-fluoroethyl)-8-methoxy-4-oxo-1,4-dihydroquinoline-3-carboxylato-$O^3,O^4$]boron was added to the reaction mixture at an internal temperature of 33.8 to 34.1° C., and the reaction mixture was stirred at an internal temperature of about 35° C. for 4 hours. A solution mixture of 240 g of methanesulfonic acid and 2.40 L of ice water was added to the reaction mixture, and the reaction mixture was stirred at an internal temperature of about 35° C. for 1 hour. 4.32 L of ethyl acetate was added to the reaction mixture. The resultant mixture was stirred for 10 minutes, and an aqueous layer was separated. A solution mixture of 120 g of methanesulfonic acid and 1.20 L of ice water was added to an organic layer. The resultant mixture was stirred for 10 minutes, and then an aqueous layer was separated.

The aqueous layers were combined and cooled, and a 2 mol/L sodium hydroxide solution was added thereto at an internal temperature of 15° C. or less to obtain a solution mixture having a pH of 7.3. 5.76 L of an ethyl acetate/acetone (5:1) solvent mixture was added to the obtained solution mixture. The resultant mixture was stirred for 10 minutes, and an organic layer was separated. 4.80 L of an ethyl acetate/acetone (5:1) solvent mixture was added to an aqueous layer. The resultant mixture was stirred for 10 minutes, and an organic layer was separated. The organic layers were combined, washed with 2.40 L of ice water, and concentrated under reduced pressure to obtain 177 g of a yellow powder of crude crystals of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid.

REFERENCE EXAMPLE 4

Bis(acetato-O)-[6,7-difluoro-1-(2-fluoroethyl)-8-methoxy-4-oxo-1,4-dihydroquinoline-3-carboxylato-$O^3,O^4$]boron 86.4 g (1.40 mol) of boric acid (for production of a catalyst) was added to 17.9 L (190 mol) of acetic anhydride in a nitrogen atmosphere, and the mixture was heated and stirred at 70.0 to 77.7° C. for 30 minutes. Then the mixture was cooled to an internal temperature of 24.7° C. (warm water temperature setting: 23.0° C.). Then boric acid was added in four portions to the solution mixture. More specifically, 842 g (13.6 mol) of boric acid (the first portion) was added to the solution mixture, and the resultant mixture was stirred at 24.7 to 27.4° C. for 30 minutes. Then 842 g (13.6 mol) of boric acid (the second portion) was added to the solution mixture, and the resultant mixture was stirred at 24.3 to 26.3° C. for 30 minutes. 842 g (13.6 mol) of boric acid (the third portion) was added to the solution mixture, and the resultant mixture was stirred at 24.3 to 26.8° C. for 30 minutes. 842 g (13.6 mol) of boric acid (the fourth portion) was added to the solution mixture, and the resultant mixture was stirred at 25.1 to 28.3° C. for 30 minutes. The solution mixture was stirred at 50.0 to 54.9° C. for 30 minutes to obtain a boric acid triacetate adjusting solution.

4.60 kg (14.0 mol) of 6,7-difluoro-1-(2-fluoroethyl)-8-methoxy-4-oxo-1,4-dihydroquinoline-3-carboxylic acid ethyl ester was added to the boric acid triacetate adjusting solution to obtain a reaction preparation solution, and this solution was stirred at 53.7 to 56.9° C. for three hours. The reaction preparation solution was cooled to 30.0° C. and left to stand overnight at room temperature. The reaction preparation solution was heated to 55.0° C. to dissolve precipitates, and 13.8 L of acetone was added thereto to obtain a reaction mixture (1).

Separately, 161 L of water and 28.2 L (464 mol) of ammonia water (28%) were mixed in a nitrogen atmosphere, and the mixture was cooled to 1.6° C. The above-prepared reaction mixture (1) was added to the mixture, and the resultant mixture was washed with 9.20 L of acetone to obtain a solution for obtaining crude crystals. The solution for obtaining crude crystals was cooled to 15.0° C. and stirred at 6.2 to 15.0° C. for one hour. Precipitated crystals were separated by filtration and washed with 46.0 L of water to obtain 9.07 kg of wet crude crystals. The wet crude crystals were dried under reduced pressure at a temperature setting of 65.0° C. for about 16 hours to obtain 5.89 kg of crude crystals.

29.5 L of acetone and the crude crystals were mixed in a nitrogen atmosphere, and the obtained solution mixture was heated for dissolution (dissolution temperature: 52.6° C.). In the heating, 58.9 L of diisopropyl ether was added dropwise to the solution mixture until crystallization occurred (the amount of dropwise addition: 10.0 L, 52.8->48.7° C., crystallization temperature: 49.0° C.). After the occurrence of crystallization was observed, the solution mixture was stirred at 49.0 to 50.1° C. for 15 minutes, and the remaining diisopropyl ether was added dropwise to the solution mixture (50.1->46.4° C.), and the resultant mixture was stirred at 46.7 to 51.7° C. for 15 minutes. The solution mixture was cooled to 15° C. and stirred at 8.1 to 15.0° C. for 30 minutes. Precipitated crystals were separated by filtration and washed with 5.89 L of acetone and 11.8 L of diisopropyl ether to obtain 6.19 kg of wet crystals. The wet crystals were dried under reduced pressure at a warm water temperature setting of 65.0° C. for about 20 hours to obtain 5.42 kg of bis(acetato-O)-[6,7-difluoro-1-(2-fluoroethyl)-8-methoxy-4-oxo-1,4-dihydroquinoline-3-carboxylato-$O^3,O^4$]boron (yield: 90.4%).

Melting point: 183 to 185° C. (dec).
Elemental analysis (%): as $C_{17}H_{15}BF_3NO_8$
Calcd.: C, 47.58; H, 3.52; N, 3.26.
Measured: C, 47.91; H, 3.44; N, 3.04.
$^1$H-NMR (CDCl$_3$, 400 MHz) δ: 2.04 (6H, s), 4.22 (3H, d, J=2.4 Hz), 4.88 (2H, dt, J=47.0, 4.4 Hz), 5.21 (2H, dt, J=24.9, 4.4 Hz), 8.17 (1H, t, J=8.8 Hz), 9.11 (1H, s).
ESI MS (positive) m/z: 430 (M+H)$^+$.
IR (KBr) cm$^{-1}$: 3080, 1703.

REFERENCE EXAMPLE 5

7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt 25.0 L of dimethylsulfoxide, 9.72 L (69.9 mol) of triethylamine, and 2.96 kg (12.8 mol) of (3R,4S)-3-cyclopropylaminomethyl-4-fluoropyrrolidine were mixed in a nitrogen atmosphere to obtain a reaction mixture, and the reaction mixture was stirred at 23.3 to 27.5° C. for 15 minutes. 5.00 kg (11.7 mol) of bis(acetato-O)-[6,7-difluoro-1-(2-fluoroethyl)-8-methoxy-4-oxo-1,4-dihydroquinoline-3-carboxylato-$O^3,O^4$] boron was added to the reaction mixture at 26.4 to 28.1° C., and the reaction mixture was stirred at 23.7 to 28.3° C. for 2 hours. 100 L of ethyl acetate was added to the reaction mixture, and 100 L of water was added thereto. Then a solution of 800 g of sodium hydroxide (an amount giving a 2 mol/L solution) in 10.0 L of water was added to the reaction mixture. The reaction mixture was stirred for 5 minutes, and an aqueous layer was separated. 100 L of ethyl acetate was added to the aqueous layer. The resultant mixture was stirred for 5 minutes, and an ethyl acetate layer was separated.

The ethyl acetate layer was combined, and 100 L of water was added thereto. The resultant mixture was stirred for 5 minutes and left to stand, and an aqueous layer was discarded. Then the ethyl acetate layer was evaporated under reduced pressure. The obtained residue was dissolved in 50.0 L of 2-propanol and the resultant solution was left to stand overnight at room temperature. A solution of 4.37 L (52.4 mol) of hydrochloric acid in 21.8 L of water (an amount giving a 2 mol/L solution) was added to the solution, and the resultant mixture was stirred at 23.6 to 26.4° C. for 30 minutes. The mixture was heated at an external temperature of 55.0° C. for dissolution (dissolution was observed at 48.3° C.) and then cooled for crystallization. The mixture was stirred at 39.8 to 41.4° C. for 30 minutes, then cooled (approximate temperature settings: 7.0° C. until 20.0° C. and −10.0° C. below 20.0° C.), and stirred at 4.4 to 10.0° C. for 1 hour. Precipitated crystals were separated by filtration and washed with 50 L of 2-propanol to obtain 7.07 kg of wet crude crystals of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt.

EXAMPLE 1

7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt (crystals A)

9.57 kg of the crude 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt obtained in Reference Example 1 was added to a solvent mixture of 60 L of ethanol and 10.8 L of purified water, and the mixture was heated for dissolution. The solution was filtered through a filter and washed with a solvent mixture of 24.0 L of ethanol and 1.20 L of purified water. After dissolution was confirmed, 96.0 L of heated ethanol (99.5) was added to the solution at 71.2 to 72.6° C. Then the resultant solution was cooled (warm water temperature setting: 60.0° C.). After the occurrence of crystallization was observed (crystallization temperature: 61.5° C.), the mixture was stirred at 59.4 to 61.5° C. for 30 minutes. The mixture was cooled in stages (the warm water temperature setting at above 50.0° C. was 40.0° C.; the warm water temperature setting at above 40.0° C. was 30.0° C.; the warm water temperature setting at above 30.0° C. was 20.0° C.; the temperature setting at above 20.0° C. was 7.0° C.; the temperature setting at above 15.0° C. was −10.0° C.; and then the mixture was left to stand) and then stirred at 4.8 to 10.0° C. for one hour. Precipitated crystals were separated by filtration and washed with 30.0 L of ethanol to obtain 5.25 kg of wet crystals of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt. The filtration rate of the precipitated crystals was high, and the crystals could be easily filtrated even in an industrial scale. The obtained crystals was dried under reduced pressure at a temperature setting of 50.0° C. for about 13 hours to obtain 4.83 kg of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt (crystals A) (yield: 72.6%).

The results of powder X-ray diffraction are shown in FIG. 1. As can be seen in FIG. 1, peaks appeared at 4.9°, 10.8°, 12.9°, 18.2°, 21.7°, 24.7°, and 26.4°, and characteristic peaks were found at 10.8°, 12.9°, and 24.7°.

Figure 4:
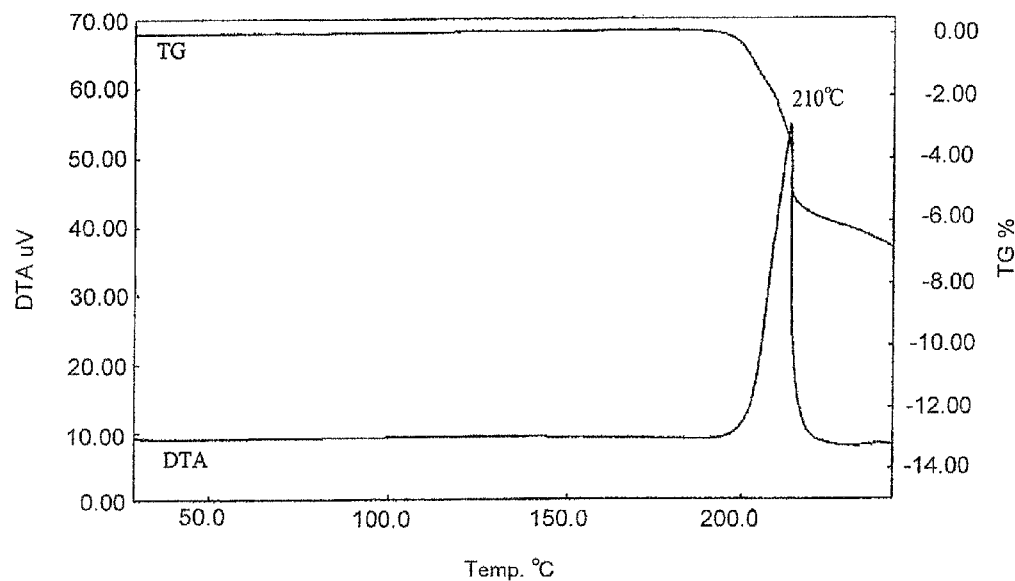
FIG. 4 shows thermal analysis (TG/DTA) chart of the hydrochloride salt of the compound (1) (crystals A).

The results of thermal analysis (TG/DTA) are shown in FIG. 4. As can be seen in FIG. 4, in differential thermal analysis (DTA), only an exothermic peak due to decomposition appeared at 210° C., and no other endothermic peaks and exothermic peaks were observed. In thermogravimetric (TG) analysis, no weight loss was observed until 150° C., at least 100° C.

Elemental analysis (%): as $C_{21}H_{24}F_3N_3O_4 \cdot HCl$
Calcd.: C, 53.00; H, 5.30; N, 8.83.
Measured: C, 53.04; H, 5.18; N, 8.83.
$^1$H-NMR (DMSO-$d_6$, 400 MHz) δ (ppm): 0.77-0.81 (2H, m), 0.95-1.06 (2H, m), 2.80-2.90 (2H, m), 3.21-3.24 (1H, m), 3.35-3.39 (1H, m), 3.57 (3H, s), 3.65-3.78 (3H, m), 4.13 (1H, dd, J=41.8, 13.1 Hz), 4.64-4.97 (3H, m), 5.14 (1H, dd, J=32.7, 15.6 Hz), 5.50 (1H, d, J=53.7 Hz), 7.80 (1H, d, J=13.7 Hz), 8.86 (1H, s), 9.44 (2H, br s), 15.11 (1H, br s).
ESI MS(positive) m/z: 440 (M+H)$^+$.

EXAMPLE 2

7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt hydrate (crystals B)

30.0 g (63.0 mmol) of the 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt obtained in Reference Example 1 was added to a solvent mixture of 600 mL of 2-propanol and 90.0 mL of water, and the mixture was heated for dissolution (internal temperature: 72° C.). Then the solution was cooled. After the occurrence of crystallization was observed (internal temperature: 49° C.), the mixture was stirred at around the crystallization temperature (internal temperature: 48 to 49° C.) for 5 minutes. The solution was heated from the crystallization temperate until the internal temperature increased about 10° C. and stirred at this temperature for 30 minutes (internal temperature: 48 to 60° C.). The solution was gradually cooled (cooled by about 1° C. per minute) and stirred at 10° C. or less for 1 hour (internal temperature: 2 to 10° C.). Precipitated crystals were filtrated and washed with a solvent mixture of 143 mL of 2-propanol and 7.5 mL of water to obtain 34.5 g of a white powder of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt hydrate (crystals B).

Figure 2:
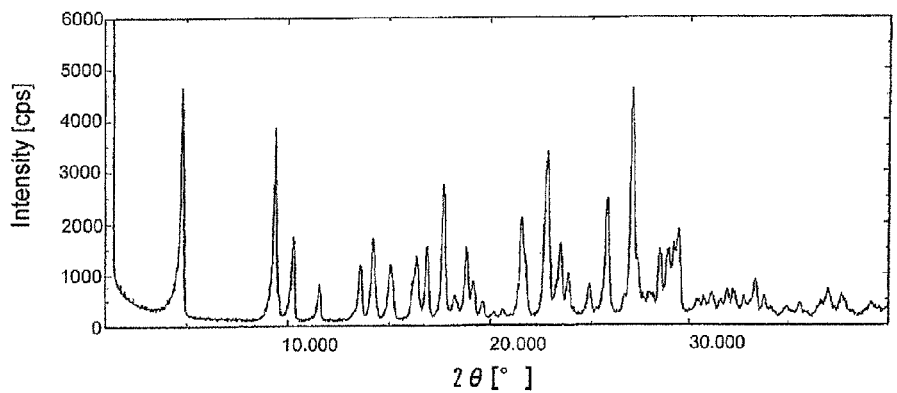
FIG. 2 shows a powder X-ray diffraction pattern of a hydrate of the hydrochloride salt of the compound (1) (crystals B).

The results of powder X-ray diffraction are shown in FIG. 2. As can be seen in FIG. 2, peaks appeared at 4.8°, 9.4°, 17.7°, 22.8°, 25.8°, and 27.0°, and characteristic peaks were found at 9.4° and 17.7°.

Figure 5:
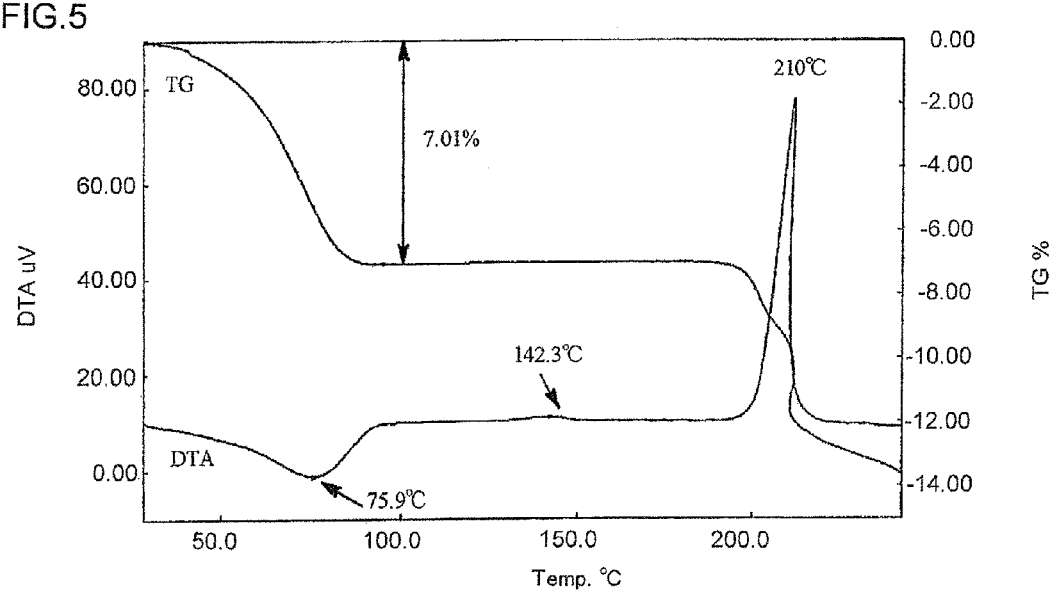
FIG. 5 shows thermal analysis (TG/DTA) chart of the hydrate of the hydrochloride salt of the compound (1) (crystals B).

The results of thermal analysis are shown in FIG. 5. As can be seen in FIG. 5, in the differential thermal analysis (DTA), an endothermic peak due to dehydration was observed when the temperature increased from room temperature to 100° C. (at 75.9° C. in FIG. 5), and exothermic peaks were observed at 142.3° C. and 210° C. In the thermogravimetric (TG) analysis, a weight loss of 7.01% was observed until 100° C.

The measurement value in Karl Fischer water content determination was 7%.

The mole ratio of the compound:water was 1:2 calculated based on the measurement value in Karl Fischer water content determination. Additionally, the weight loss until 100° C. in the thermogravimetric (TG) analysis corresponded to the measurement value in Karl Fischer water content determination, and it was clearly observed the endothermic peak when the temperature increased from room temperature to about 100° C. in the differential thermal analysis (DTA). That is, it is realized that the desorption of crystalline water from the crystalline structure caused by heating from room temperature to about 100° C. was occurred, and the obtained crystal was identified as the hydrated crystals.

$^1$H NMR (DMSO-$d_6$, 400 MHz) δ (ppm): 0.77-0.81 (2H, m), 0.98-1.00 (2H, m), 2.79-2.93 (2H, m), 3.22 (1H, dd, J=8.4, 12.2 Hz), 3.58 (3H, s), 3.65-3.81 (3H, m), 4.13 (1H, dd, J=13.2, 42.1 Hz), 4.81-4.97 (2H, m), 5.15 (1H, dd, J=15.7, 32.8 Hz), 5.55 (1H, d, J=53.8 Hz), 7.79 (1H, dd, J=2.4, 13.2 Hz), 8.85 (s, 1H), 9.56 (2H, brs), 15.07 (1H, brs).

EXAMPLES 3 TO 7

Hydrochloride salts of the compound (1) were obtained as in Example 2 except that solvent ratio and solvent amount conditions shown in TABLE 1 were used. TABLE 1 shows the values of water activity and the types of obtained crystals.

TABLE 1

| | RATIO OF CRYSTALLIZATION SOLVENT | AMOUNT OF SOLVENT (AMOUNT OF SOLVENT PER 1 g OF CRUDE HYDROCHLORIDE SALT) | WATER ACTIVITY VALUE | CRYSTAL |
|---|---|---|---|---|
| EXAMPLE 1 | EtOH:H$_2$O = 15:1 | 32 mL | 0.33 | CRYSTALS A |
| EXAMPLE 3 | EtOH:H$_2$O = 10:1 | 22 mL | 0.43 | CRYSTALS A |
| EXAMPLE 4 | EtOH:H$_2$O = 41:9 | 4 mL | 0.67 | CRYSTALS B |
| EXAMPLE 2 | IPA:H$_2$O = 20:3 | 23 mL | 0.77 | CRYSTALS B |
| EXAMPLE 5 | IPA:H$_2$O = 10:1 | 22 mL | 0.67 | CRYSTALS B |
| EXAMPLE 6 | IPA:H$_2$O = 94:6 | 50 mL | 0.52 | CRYSTALS B |
| EXAMPLE 7 | IPA:H$_2$O = 97:3 | 100 mL | 0.33 | CRYSTALS A |

EtOH: ETHANOL,
IPA: 2-PROPANOL

EXAMPLE 8

7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt hydrate (crystals B)

1 g of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt (crystals A) was spread over a petri dish and placed in a desiccator in which a saturated potassium sulfate solution had been placed. The crystals A was stored at 25° C. for 1 week to obtain 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt hydrate (crystals B).

EXAMPLE 9

7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid methanesulfonate salt 3.36 L of acetone was added to 178 g of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid synthesized according to Reference Example 3, and the mixture was heated for dissolution. 0.48 L of an acetone solution of 59.1 g of methanesulfonic acid was added dropwise to the solution at an internal temperature of around 40° C. (the solution obtained is hereinafter referred to as a solution mixture). The solution mixture was stirred at an internal temperature of around 40° C. for 0.5 hours. The solution mixture was cooled and stirred at an internal temperature of 10° C. or less for 0.5 hours. Precipitated crystals were separated by filtration, washed with 1.44 L of acetone, and dried at 50° C. under reduced pressure for 2 hours to obtain 198 g of crude 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid methanesulfonate salt.

1.98 L of a solvent mixture of acetone and water (5:1) was added to 198 g of the crude product, and the mixture was heated for dissolution. The solution was filtrated through a filter, and the vessel was washed with 2.96 L of acetone. The filtrate was combined with the washings, and the mixture was stirred at room temperature. After crystals were precipitated, the mixture was stirred for 15 minutes, heated, and stirred at an internal temperature of 35 to 41° C. for 0.5 hours. The mixture was cooled and stirred at an internal temperature of 10° C. or less for 0.5 hours. Precipitated crystals were separated by filtration and washed with 0.99 L of acetone. And the wet crystals (136 g) were dried under reduced pressure at 40° C. for 19 hours and then at 50° C. for about 4 hours to obtain 133 g of crystals of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid methanesulfonate salt.

Figure 3:
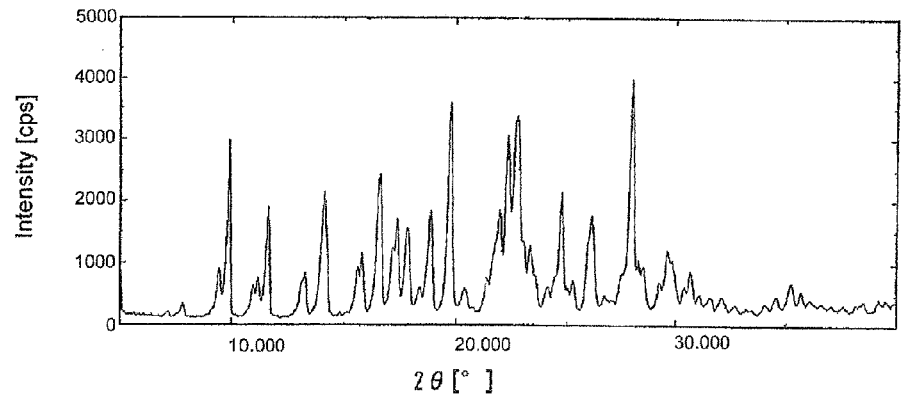
FIG. 3 shows a powder X-ray diffraction pattern of the methanesulfonate salt of the compound (1).

The results of powder X-ray diffraction are shown in FIG. 3. As can be seen in FIG. 3, peaks appeared at 9.9°, 14.1°, 16.6°, 19.8°, 22.3°, and 28.0°, and characteristic peaks were observed at 9.9°, 14.1°, and 28.0°.

Figure 6:
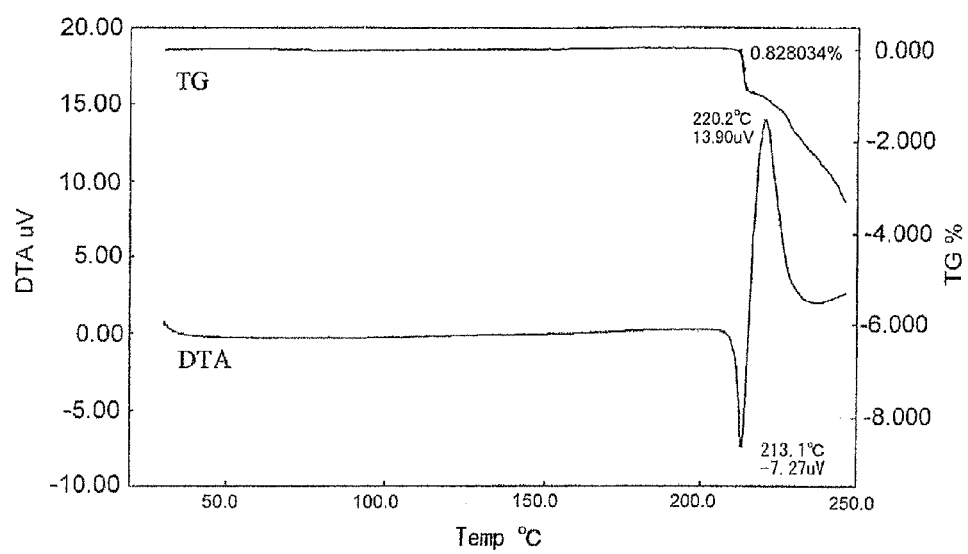
FIG. 6 shows thermal analysis (TG/DTA) chart of the methanesulfonate salt of the compound (1).

The results of thermal analysis (TG/DTA) are shown in FIG. 6. As can be seen in FIG. 6, in the differential thermal analysis (DTA), an endothermic peak due to fusion was observed at 213.1° C., and an exothermic peak due to decomposition was observed at 220.2° C. No other endothermic peaks and exothermic peaks were observed. In the thermogravimetric (TG) analysis, no weight loss was observed until 200° C., at least 100° C.

Melting point (hot plate method): 207 to 210° C. (decomposition)

$[\alpha]_D^{28}$ −176 (c 1.0, $H_2O$)

IR (KBr method); 1727, 1626, 1466, 1227, 1059 $cm^{-1}$

Elemental analysis (%): as $C_{21}H_{24}F_3N_3O_4 \cdot CH_4O_3S$

Calcd.: C, 49.34; H, 5.27; N, 7.85.

Measured: C, 49.49; H, 5.15; N, 7.62.

$^1$H NMR (DMSO-$d_6$, 400 MHz) δ (ppm): 0.78-0.92 (4H, m), 2.35 (3H, d, J=1.7 Hz), 2.73-2.87 (2H, m), 3.28 (1H, dd, J=12.8, 7.0 Hz), 3.42 (1H, dd, J=13.0, 6.6 Hz), 3.58 (3H, s), 3.65-3.76 (3H, m), 4.13 (1H, ddt, J=42.1, 12.9, 2.8 Hz), 4.66-4.97 (3H, m), 5.08-5.22 (1H, m), 5.46 (1H, d, J=53.6 Hz), 7.80 (1H, d, J=13.6 Hz), 8.78-8.93 (3H, m), 15.07 (1H, brs).

ESI MS(positive) m/z: 440 (M+H)$^+$.

EXAMPLE 10

7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt (crystals A)

7.07 kg of the crude 7-{(3S,4S)-3-[(cyclopropylamino) methyl]-4-fluoropyrrolidine-1-yl}-6-fluoro-1-(2-fluoroethyl)-8-methoxy-4-oxo-1,4-dihydroquinoline-3-carboxylic acid hydrochloride salt obtained in Reference Example 5 was added to a solvent mixture of 50 L of ethanol and 9.0 L of purified water, and the mixture was heated for dissolution. The obtained solution was filtrated through a filter and washed with a solvent mixture of 20.0 L of ethanol and 1.0 L of purified water. After dissolution was confirmed, 80.0 L of heated ethanol (99.5) was added to the solution at 70.6 to 71.4° C. The solution was cooled (warm water temperature setting: 60.0° C.). After the occurrence of crystallization was observed (crystallization temperature: 61.4° C.), the mixture was stirred at 60.0 to 61.4° C. for 30 minutes. The mixture was cooled in stages (cooled until 50.0° C. with a warm water temperature setting of 40.0° C., cooled until 40.0° C. with a warm water temperature setting of 30.0° C., cooled until 30.0° C. with a warm water temperature setting of 20.0° C., cooled until 20.0° C. with a temperature setting of 7.0° C., cooled until 15.0° C. with a temperature setting of −10.0° C., and then left to stand) and then stirred at 1.2 to 10.0° C. for one hour. Precipitated crystals were separated by filtration and washed with 25.0 L of ethanol to obtain 4.52 kg of wet crystals of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt. The wet crystals were dried at a temperature setting of 50.0° C. under reduced pressure for about 14 hours to obtain 4.07 kg of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt (crystals A) (yield: 73.4%).

Elemental analysis (%): as $C_{21}H_{24}F_3N_3O_4 \cdot HCl$

Calcd.: C, 53.00; H, 5.30; N, 8.83.

Measured: C, 52.80; H, 5.35; N, 8.82.

$^1$H NMR (DMSO-$d_6$, 400 MHz) δ (ppm): 0.71-0.86 (2H, m), 0.90-1.07 (2H, m), 2.73-2.98 (2H, m), 3.15-3.29 (1H, m), 3.30-3.45 (1H, m), 3.58 (3H, s), 3.63-3.83 (3H, m), 4.13 (1H, dd, J=42.1, 13.2 Hz), 4.64-5.00 (3H, m), 5.15 (1H, dd, J=32.8, 15.7 Hz), 5.52 (1H, dt, J=53.8, 2.9 Hz), 7.80 (1H, d, J=13.7 Hz), 8.86 (1H, s), 9.55 (2H, brs), 15.11 (1H, brs).

ESI MS (positive) m/z: 440 (M+H)$^+$.

TEST EXAMPLE 1

Storage stability test on crystals of hydrochloride salt (crystals A), crystals of hydrochloride salt hydrate (crystals B), crystals of hydrochloride salt (crystals C), and crystals of methanesulfonate salt After the crystals of hydrochloride salt (crystals A), crystals of hydrochloride salt hydrate (crystals B), crystals of hydrochloride salt (crystals C), and crystals of methanesulfonate salt of the compound (1) were stored in a closed or open condition at 40° C. and a relative humidity of 75% with opaque containers, the amounts of these crystals were measured by HPLC.

HPLC conditions: a column, which is Inertsil ODS-3V manufactured by GL Sciences Inc., and has an inner diameter of 4.6 mm, a length of 15 cm, and a particle diameter of 5 μm, was used. A mobile phase used was a mixture of a mobile phase A and a mobile phase B. Diluted phosphoric acid (1->1000) was used as the mobile phase A, and methanol for liquid chromatography was used as the mobile phase B. The ratio of the mobile phase A was changed from 65% to 70% at 0 to 10 minutes, from 70% to 65% at 10 to 20 minutes, and from 65% to 20% at 20 to 40 minutes and held at 20% at 40 to 45 minutes to control the concentration gradient, and the mobile phase was fed at a flow rate of 1 mL per minute. The measurement wavelength used was 294 nm.

TABLE 2 shows the results of the analysis of the amounts of remaining unaltered crystals at different times when the crystals of hydrochloride salt (crystals A), the crystals of hydrochloride salt hydrate (crystals B), the crystals of hydrochloride salt (crystals C), the crystals of methanesulfonate salt, and the free crystals were stored under the conditions of 40° C. and 75% RH.

TABLE 2

Storage stability (40° C./75% RH) of crystals of hydrochloride salt (crystals A), crystals of hydrochloride salt hydrate (crystals B), crystals of hydrochloride salt (crystals C), crystals of methanesulfonate salt, and free crystals.

| | | 2 WEEKS | | 4 WEEKS | |
|---|---|---|---|---|---|
| CRYSTAL FORM | INITIAL | OPEN CONDITION | CLOSED CONDITION | OPEN CONDITION | CLOSED CONDITION |
| CRYSTALS A | 99.52 | ND | ND | 99.51 | 99.52 |
| CRYSTALS B | 99.59 | ND | ND | 99.64 | 99.65 |
| CRYSTALS C | 99.75 | 99.47 | 99.37 | ND | ND |
| CRYSTALS OF METHANESULFONATE SALT | 95.18 | ND | ND | 95.89 | 96.09 |
| FREE CRYSTALS | 95.18 | 95.27 | 95.13 | 95.35 | 95.00 |

ND = No data

As is clear from TABLE 2, in the crystals C, the amount of unaltered crystals was found to decrease at 2 weeks, and therefore the storage stability was not high. However, in the crystals A, the crystals B, and the crystals of methanesulfonate salt, no change in the amount of unaltered crystals was observed at 4 weeks, and therefore, like the free crystals, they were stable.

TEST EXAMPLE 2

Test of storage stability against light on crystals of hydrochloride salt (crystals A), crystals of methanesulfonate salt, and free crystals TABLE 3 shows the results of analysis of the amounts of remaining unaltered crystals at different times when the crystals A, the crystals of methanesulfonate salt, and the free crystals were stored under irradiation using a D65 fluorescent lamp.

TABLE 3

Storage stability against light (D65 irradiation) of CRYSTALS OF hydrochloride salt (crystals A), CRYSTALS OF methanesulfonate salt, and free crystals

| CRYSTAL FORM | INITIAL | TOTAL IRRADIATION AMOUNT(lx · hrs) | | | | |
|---|---|---|---|---|---|---|
| | | 110,000 | 220,000 | 530,000 | 860,000 | 1,280,000 |
| CRYSTALS A | 98.68 | 97.74 | 97.43 | 97.32 | 96.32 | 91.33 |
| CRYSTALS OF METHANESULFONATE SALT | 98.83 | 98.01 | 97.5 | 96.91 | 95.37 | 95.11 |
| FREE CRYSTALS | 96.12 | 77.71 | 75.31 | 66.34 | 49.82 | 44.85 |

In the free crystals, the amount of unaltered crystals was found to significantly decrease even at 110,000 lx·hrs. On the other hand, in the crystals A and the crystals of methanesulfonate salt, almost no change was observed at that irradiation amount. The amounts of the crystals A and the crystals of methanesulfonate salt were found to decrease at 1,280,000 lx·hrs. However, the reduction in the amount of the free crystals at 1,280,000 lx·hrs was 50% or larger. Therefore, the stability of the crystals A and the crystals of methanesulfonate salt were found to be significantly improved.

TEST EXAMPLE 3

Test of solubility of crystals of hydrochloride salt (crystals A), crystals of hydrochloride hydrate (crystals B), crystals of methanesulfonate salt, and free crystals in water TABLE 4 shows the solubilities of the crystals of hydrochloride salt (crystals A), the crystals of hydrochloride salt hydrate (crystals B), the crystals of methanesulfonate salt, and the free crystals in water.

TABLE 4

| CRYSTAL FORM | SOLUBILITY(mg/mL) |
|---|---|
| CRYSTALS A | >10 |
| CRYSTALS B | >10 |
| CRYSTALS OF METHANESULFONATE SALT | >10 |
| FREE CRYSTALS | <1 |

The solubility of the free crystals was 1 mg/mL or less. On the other hand, the solubilities of the crystals A, crystals B, and crystals of methanesulfonate salt were 10 mg/mL or larger, and the solubilities in water were clearly improved.

Industrial Applicability

The present invention can provide crystals of the hydrochloride salt, hydrochloride salt hydrate, and methanesulfonate salt of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid that is safe and not only has a strong antibacterial action but also is effective for resistant bacteria for which conventional antibacterial agent are less effective. These crystals have high solubility in water and high storage stability. According to the methods of the invention, the crystals of the hydrochloride salt, hydrochloride salt hydrate, and methanesulfonate salt can be supplied independently in a stable manner. These hydrochloride salt, hydrochloride salt hydrate, and methanesulfonate salt can be selectively used as pharmaceuticals.

The invention claimed is:

1. A crystal of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt, having powder X-ray diffraction peaks at diffraction angles 2θ of 10.8°±0.2°, 12.9°±0.2°, and 24.7°±0.2°.

2. The crystal according to claim 1, having powder X-ray diffraction peaks at diffraction angles 2θ of 4.9°±0.2°, 10.8°±0.2°, 12.9°±0.2°, 18.2°±0.2°, 21.7°±0.2°, 24.7°±0.2°, and 26.4°±0.2°.

3. The crystal according to claim 1, having a powder X-ray diffraction pattern identical to a powder X-ray diffraction pattern shown in FIG. 1.

4. The crystal according to claim 1, wherein, in differential thermal analysis (DTA), an exothermic peak appears only in the vicinity of 210° C., and in thermogravimetric (TG) analysis, no weight loss occurs below 100° C.

5. A crystal of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid hydrochloride salt hydrate, having powder X-ray diffraction peaks at diffraction angles 2θ of 9.4°±0.2° and 17.7°±0.2°.

6. The crystal according to claim 5, having powder X-ray diffraction peaks at diffraction angles 2θ of 4.8°±0.2°, 9.4°±0.2°, 17.7°±0.2°, 22.8°±0.2°, 25.8°±0.2°, and 27.0°±0.2°.

7. The crystal according to claim 5, having a powder X-ray diffraction pattern identical to a powder X-ray diffraction pattern shown in FIG. 2.

8. The crystal according to claim 5, wherein, in differential thermal analysis (DTA), an endothermic peak appears between room temperature and 100° C., and an exothermic peak appears in the vicinity of 140° C., and in thermogravimetric (TG) analysis, weight loss until 100° C. is about 7%.

9. The crystal according to claim 5, wherein a water content determined by a Karl Fischer water content determination is about 7%.

10. A crystal of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid methanesulfonate salt, having powder X-ray diffraction peaks at diffraction angles 2θ of 9.9°±0.2°, 14.1°±0.2°, and 28.0°±0.2°.

11. The crystal according to claim 10, having powder X-ray diffraction peaks at diffraction angles 2θ of 9.9°±0.2°, 14.1°±0.2°, 16.6°±0.2°, 19.8°±0.2°, 22.3°±0.2°, and 28.0°±0.2°.

12. The crystal according to claim 10, having a powder X-ray diffraction pattern identical to a powder X-ray diffraction pattern shown in FIG. 3.

13. The crystal according to claim 10, wherein, in differential thermal analysis (DTA), an endothermic peak appears in the vicinity of 213° C., and an exothermic peak appears only in the vicinity of 220° C., and in thermogravimetric (TG) analysis, no weight loss occurs below 100° C.

14. A pharmaceutical composition comprising the crystal according to claim 1, and a pharmaceutically acceptable carrier, solvent or diluent.

15. An antibacterial agent comprising the crystal according to claim 1 as an active pharmaceutical ingredient, or prepared by incorporating the crystal according to claim 1 as an active pharmaceutical ingredient.

16. The antibacterial agent according to claim 15, wherein the antibacterial agent is an oral dosage formulation.

17. The antibacterial agent according to claim 15, wherein the antibacterial agent is an injection.

18. A method for producing the crystal according to claim 1, comprising:
adding hydrochloric acid to a 2-propanol solution of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid to obtain a crude hydrochloride salt; and
crystallizing the obtained crude hydrochloride salt with hydrous ethanol having a water activity of less than 0.5 or hydrous 2-propanol having a water activity of less than 0.5.

19. A crystal obtained by: adding hydrochloric acid to a 2-propanol solution of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid to obtain a crude hydrochloride salt; and crystallizing the obtained crude hydrochloride salt with hydrous ethanol having a water activity of less than 0.5 or hydrous 2-propanol having a water activity of less than 0.5.

20. A method for producing the crystal according to claim 5, comprising:
adding hydrochloric acid to a 2-propanol solution of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid to obtain a crude hydrochloride salt; and
crystallizing the obtained crude hydrochloride salt with hydrous ethanol having a water activity of 0.5 or higher or hydrous 2-propanol having a water activity of 0.5 or higher.

21. A crystal obtained by: adding hydrochloric acid to a 2-propanol solution of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid to obtain a crude hydrochloride salt; and crystallizing the obtained crude hydrochloride salt with hydrous ethanol having a water activity of 0.5 or higher or hydrous 2-propanol having a water activity of 0.5 or higher.

22. A method of producing the crystal according to claim 10, comprising:
adding methanesulfonic acid to an acetone solution of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid to obtain a crude methanesulfonate salt; and
crystallizing the obtained crude methanesulfonate salt with hydrous acetone.

23. A crystal obtained by: adding methanesulfonic acid to an acetone solution of 7-{(3S,4S)-3-[(cyclopropylamino)methyl]-4-fluoropyrrolidine-1-yl}-6-fluoro-1-(2-fluoroethyl)-8-methoxy-4-oxo-1,4-dihydroquinoline-3-carboxylic acid to obtain a crude methanesulfonate salt; and crystallizing the obtained crude methanesulfonate salt with hydrous acetone.

24. The crystal according to claim 2, having a powder X-ray diffraction pattern identical to a powder X-ray diffraction pattern shown in FIG. 1.

25. The crystal according to claim 2, wherein, in differential thermal analysis (DTA), an exothermic peak appears only in the vicinity of 210° C., and in thermogravimetric (TG) analysis, no weight loss occurs below 100° C.

26. The crystal according to claim 3, wherein, in differential thermal analysis (DTA), an exothermic peak appears only in the vicinity of 210° C., and in thermogravimetric (TG) analysis, no weight loss occurs below 100° C.

27. The crystal according to claim 24, wherein, in differential thermal analysis (DTA), an exothermic peak appears only in the vicinity of 210° C., and in thermogravimetric (TG) analysis, no weight loss occurs below 100° C.

28. The crystal according to claim 6, having a powder X-ray diffraction pattern identical to a powder X-ray diffraction pattern shown in FIG. 2.

29. The crystal according to claim 6, wherein, in differential thermal analysis (DTA), an endothermic peak appears between room temperature and 100° C., and an exothermic peak appears in the vicinity of 140° C., and in thermogravimetric (TG) analysis, weight loss until 100° C. is about 7%.

30. The crystal according to claim 7, wherein, in differential thermal analysis (DTA), an endothermic peak appears between room temperature and 100° C., and an exothermic peak appears in the vicinity of 140° C., and in thermogravimetric (TG) analysis, weight loss until 100° C. is about 7%.

31. The crystal according to claim 28, wherein, in differential thermal analysis (DTA), an endothermic peak appears between room temperature and 100° C., and an exothermic peak appears in the vicinity of 140° C., and in thermogravimetric (TG) analysis, weight loss until 100° C. is about 7%.

32. The crystal according to claim 6, wherein a water content determined by a Karl Fischer water content determination is about 7%.

33. The crystal according to claim 7, wherein a water content determined by a Karl Fischer water content determination is about 7%.

34. The crystal according to claim 8, wherein a water content determined by a Karl Fischer water content determination is about 7%.

35. The crystal according to claim 28, wherein a water content determined by a Karl Fischer water content determination is about 7%.

36. The crystal according to claim 29, wherein a water content determined by a Karl Fischer water content determination is about 7%.

37. The crystal according to claim 30, wherein a water content determined by a Karl Fischer water content determination is about 7%.

38. The crystal according to claim 31, wherein a water content determined by a Karl Fischer water content determination is about 7%.

39. The crystal according to claim 11, having a powder X-ray diffraction pattern identical to a powder X-ray diffraction pattern shown in FIG. 3.

40. The crystal according to claim 11, wherein, in differential thermal analysis (DTA), an endothermic peak appears in the vicinity of 213° C., and an exothermic peak appears only in the vicinity of 220° C., and in thermogravimetric (TG) analysis, no weight loss occurs below 100° C.

41. The crystal according to claim 12, wherein, in differential thermal analysis (DTA), an endothermic peak appears in the vicinity of 213° C., and an exothermic peak appears only in the vicinity of 220° C., and in thermogravimetric (TG) analysis, no weight loss occurs below 100° C.

42. The crystal according to claim 39, wherein, in differential thermal analysis (DTA), an endothermic peak appears in the vicinity of 213° C., and an exothermic peak appears only in the vicinity of 220° C., and in thermogravimetric (TG) analysis, no weight loss occurs below 100° C.

43. A pharmaceutical composition comprising the crystal according to claim 5, and a pharmaceutically acceptable carrier, solvent or diluent.

44. A pharmaceutical composition comprising the crystal according to claim 10, and a pharmaceutically acceptable carrier, solvent or diluent.

45. An antibacterial agent comprising the crystal according to claim 5 as an active pharmaceutical ingredient, or prepared by incorporating the crystal according to claim 5 as an active pharmaceutical ingredient.

46. The antibacterial agent according to claim 45, wherein the antibacterial agent is an oral dosage formulation.

47. The antibacterial agent according to claim 45, wherein the antibacterial agent is an injection.

* * * * *